United States Patent [19]

Wiltse

[11] 4,230,300
[45] Oct. 28, 1980

[54] FLOW METERING AND SHUT-OFF VALVE

[75] Inventor: Harold L. Wiltse, Baldwin Park, Calif.

[73] Assignee: Mary Louise Wiltse, Baldwin Park, Calif.

[21] Appl. No.: 47,052

[22] Filed: Jun. 11, 1979

[51] Int. Cl.³ .............................................. F16K 1/04
[52] U.S. Cl. .................................. 251/205; 251/268; 251/340; 128/214 R; 128/274
[58] Field of Search .............. 251/267, 268, 205, 340; 128/274, 214 R

[56] References Cited

U.S. PATENT DOCUMENTS

| 1,291,183 | 1/1919 | Schulder | 251/268 |
| 1,398,025 | 11/1921 | James | 251/268 X |
| 3,880,401 | 4/1975 | Wiltse | 251/DIG. 4 |

*Primary Examiner*—Arnold Rosenthal
*Attorney, Agent, or Firm*—Boniard I. Brown

[57] ABSTRACT

An improved combined flow metering and shut-off valve having inner and outer valve parts which are axially movable relative to one another to effect relative axial movement of a metering valve plug on one part into and out of a metering bore on the other for regulating or blocking flow through the valve flow passage. Through the use of an interlocking collar, the inner and outer valve parts can be moved with respect to each other through rotation of the collar by one hand which rotation varies the relative axial position between the valve parts to change the metering. A seal with spaced sealing lips is provided within the valve. The lips are spaced a distance sufficient to assure that their contact areas never overlap so that contamination cannot pass into fluid flowing through the valve, which fluid is usually being introduced into a living person.

20 Claims, 4 Drawing Figures

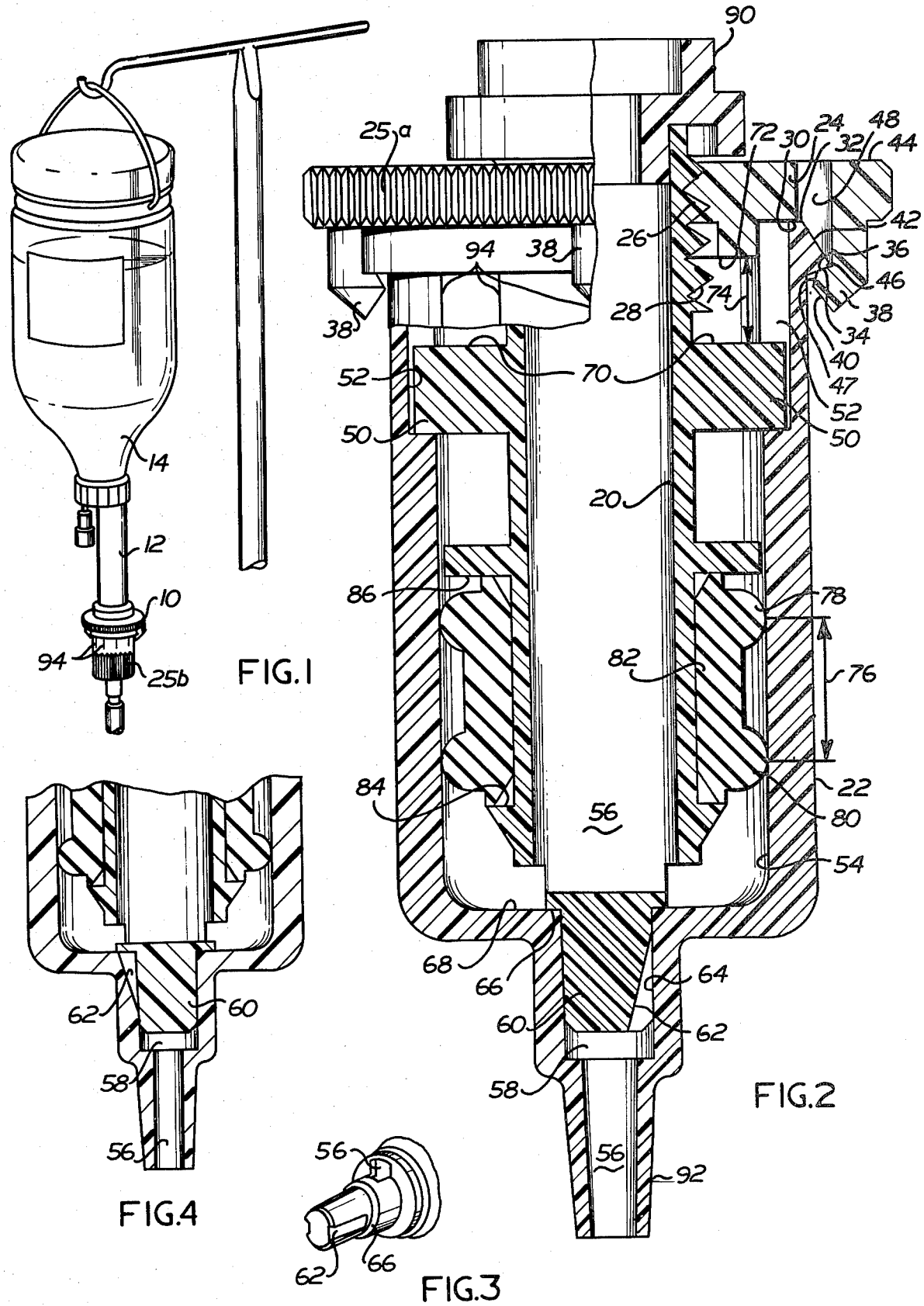

FLOW METERING AND SHUT-OFF VALVE

CROSS-REFERENCE TO RELATED PATENT

The following described invention is related to the flow metering and shut-off valve described in U.S. Pat. No. 3,880,401 which issued Apr. 29, 1975 to Harold L. Wiltse. Such patent is incorporated by reference as though fully set forth herein below.

BACKGROUND OF THE INVENTION

Medical treatment of a patient often involves intravenous injection or feeding of various solutions into the patient's body. A typical intravenous feeding system comprises a stand for supporting a container filled with an intravenous solution, a tube extending from the container fitted at its end with a needle for insertion into the patient's body, and a valve in or along the tube for regulating the rate of flow of the solution to the patient. Attending medical personnel adjust the valve to regulate the rate of flow of solution into the patient. Valves for this general purpose must regulate the solution flow with great precision, must be capable of effective sterilization, and must be sealed against the entrance of foreign matter into the solution.

Typical valves known in the prior art are shown in U.S. Pat. No. 3,685,787 to Adelberg wherein a wedge type tube squeezer device is disclosed, and in Applicant's U.S. Pat. No. 3,880,401 on which the present application is an improvement. In service such valves have proved to have certain disadvantages. Tube compression or squeezer type devices have the well-known disadvantage of variation of flow rates from set rates resulting from plastic deformation of tubes under compression, thus necessitating successive checking and resetting. They are difficult to use when adjusting the regulated flow, especially one handed, and in some instances it is possible for contamination to be introduced into the solution passing through the valve. Therefore, there has been a need for an improved valve which can be adjusted with one hand and which effectively prevents the entry of contamination into the fluid passing therethrough, while being relatively easy to manufacture and to sterilize.

BRIEF DESCRIPTION OF THE PRESENT INVENTION

The present invention provides an improved combined flow metering and shut-off valve which satisfies the above and other requirements of an intravenous flow control valve, including the provision of precise constant flow control, and hence is ideally suited for this purpose. The valve also may be used for other purposes even though it is primarily intended for intravenous flow control.

The valve has inner and outer valve parts which move axially relative to each other when a threaded collar is twisted relative to the other since the two are threadably and slidedly connected together by the collar. The inner and outer valve parts provide a flow passage including an axial flow metering bore in one part. The other part includes a flow metering valve plug which is moved into and out of the metering bore by the relative axial movement of the valve part to regulate, meter or totally block flow through the passageway. To this end, the valve plug has a tapered portion providing a flow space between the plug and wall of the metering bore. The taper of this portion is such that the effective cross-sectional flow area of the flow space therein increases as the plug retracts from the bore and decreases as the plug enters the bore. When fully inserted into the bore, the valve plug completely closes the bore to block flow through the valve flow passageway.

A single piece, radial double rib seal is provided on one valve part for sealing against a cylinderical surface of the other. The radial lips of the seal are spaced so that the axial movement of one valve part versus the other is never sufficiently large that the areas of contact overlap, and therefore contamination cannot pass the seal.

The particular valve described is an intravenous flow control valve whose outer part is a tubular barrel containing the metering bore between the barrel ends and whose inner part is a sleeve closed at one end by a wall from which the valve plug projects. Entering one end of the barrel is an axial opening which opens into one end of the metering bore and receives the closed or walled end of the valve sleeve. The opposite or outer ends of the barrel and sleeve provide coupling ends through which the valve passage extends. The barrel and sleeve are restrained from relative rotation by a pair of tangs which extend outwardly from the sleeve and are received in axial channels in the inside of the barrel. The barrel and sleeve also are connected together by a collar which is threadably connected to the sleeve and rotatably attached to the barrel. Manual rotation of the collar causes respective axial movement of the barrel and sleeve to result in movement of the valve plug into or away from the mating bore depending on the direction of rotation of the collar.

The valve plug is cylindrical and sized to fit closely in the metering bore. Entering the circumference of the plug is at least one tapered longitudinal groove or flow slot which opens through the tip of the plug. This flow slot provides a flow passage between the plug and the wall of the metering bore whose effective cross-sectional area progressively increases as the plug retracts from the bore to increase flow through the valve and progressively decreases to reduce flow as the plug enters the bore. The nose of the plug is sized to fit closely within the metering bore to close the latter completely when the plug is fully seated in the bore. The valve plug and valve barrel may also have confronting valve seating faces which abut to block flow when the valve is closed by full insertion of the valve plug into the metering bore.

Preferably the intravenous valve barrel and sleeve area constructed of plastic and the valve is designed to be disposable. The valve barrel and sleeve are sealed to one another by the aforementioned double ribbed seal to prevent leakage and entrance of foreign matter into the valve passage. The opposite ends of the valve are adapted to engage the tubing, or the lower end may be adapted to engage a reservoir which in turn engages the tubing, the reservoir being used to visually gauge the flow through the valve.

BRIEF DESCRIPTION OF THE DRAWING.

FIG. 1 is an elevational view of an intravenous feeding system embodying a valve constructed according to the present invention;

FIG. 2 is an enlarged partial cross-sectional view of the valve of FIG. 1 when closed;

FIG. 3 is a perspective detailed view of the nose of the inner valve element of FIG. 2 showing the metering grooves thereof; and FIG. 4 is a cross-sectional view of the metering portion of a modified version of the valve of FIGS. 1, 2 and 3.

DETAILED DESCRIPTION OF THE PREFERRED EMBODIMENTS

Referring to the drawing more particularly, by reference numbers, in FIG. 1, a valve 10 constructed according to the present invention, is shown in a flow line 12 metering the flow out of a fluid bottle 14 of the type normally used to provide intravenous flow into a human body. A drip chamber 12 is commonly used to indicate the flow through the flow line by observation of the rapidity of drips passing through the drip chamber.

The valve 10 has inner and outer valve parts 20 and 22, which are capable of relative axial movement when a threaded collar 24 interconnecting them is manually rotated, rotation being facilitated by serrations 25a thereon and serrations 25b on the outer valve part. The collar 24 includes threads 26 which engage similar threads 28 on the inner valve part 20. The collar 24 is restrained to rotate radially at a predetermined axial position on the outer valve part 22 by radial abutment surfaces 30 and 32 on the collar 24 and the outer valve part 22 respectively, and a frustro-conical abutment surface 34 on the part 22 and matching frustro-conical surfaces 36 on a plurality of tangs 38 which extend from the collar 24. The tangs 38 each include a second frustro-conical surface 40 which is angled to generally mate with a second frustro-conical surface 42 on the upper portion of the outer valve part 22 so that force applied on the top surface 44 of the collar 24 can snap the tangs 38 over the lip 46. A slight relief 47 may be defined between the surfaces 40 and 46 to ease this snapping action. The tangs 38 are positioned adjacent a cut out 48 in the collar 24 so that they are supported by their sides and therefore are more easily flexed for snapping engagement with the outer valve part 22.

The inner valve part 20 moves axially with respect to the outer valve part 22 in response to the rotation of the collar 24 because it is restrained from rotation by one or more tangs 50 which extend radially outwardly therefrom into mating axially aligned channels 52 in the inner surface 54 of the outer valve portion 22.

The inner and outer valve parts 20 and 22 provide a flow passageway 56 including an axially aligned flow metering bore 58 in one and a flow metering valve plug 60 in the other. The valve plug 60 is moved into and out of the metering bore 58 by the rotation of the collar 24 to regulate, meter or totally block flow through the passageway 56. The valve plug 60 has a tapered cutout portion 62 providing a flow space between the plug 60 and the wall 64 of the bore 58. The taper of this portion 62 is such that the effective cross-sectional flow area of the flow space therein increases as the plug 60 retracts from the bore 58 and decreases as the plug 60 enters the bore 58. When fully inserted in the bore 58, the valve plug 60 has a downwardly facing, radial surface 66 which engages a mating radial surface 68 on the inner surface 54 of the outer valve portion 22 to block flow through the valve flow passageway 56. As is shown in FIG. 4, the tapered cutout portion 62 can be defined in the wall defining bore 58 rather than in the plug 60.

The amount of relative axial movement between the inner and outer valve portions 20 and 22 is controlled in the closed direction by the engagement of the surfaces 66 and 68 and in the open position by engagement of the upper surfaces 70 of the tangs 50 with a downward facing radial abutment surface 72 on the collar 24. This restricted distance, shown by arrow 74, is smaller than the distance between radial ribs 78 and 80 of a seal 82 which is restrained between two facing radial abutment surfaces 84 and 86 in the inner valve portion 20. The seal 82 is ring shaped and its outwardly extending ribs 78 and 80 slide on the inner cylindrical surface 54 of the outer valve portion 22 to form a seal therewith. Since the ribs 78 and 80 are further apart than the distance that the inner valve portion 22 as shown by arrow 74, the contact areas thereof never overlap so that contamination which might otherwise be wiped there past cannot contaminate the flow from the fluid bottle 14 into the patient.

The valve parts 20 and 22 also include upper and lower connections 90 and 92 respectively to the flow line 12 of conventional configuration and indicia 94 which in cooperation with at least one of tangs indicate the relative axial position between the valve parts 20 and 22.

Thus there has been shown and described, novel flow metering valves especially adapted for intervenuous flow which fulfill all the objects and advantages sought therefore. After considering the foregoing, it will be apparent to one skilled in the art that various changes may be made in the form, construction, and arrangement of the parts of the invention without departing from the spirit and scope thereof or sacrificing its material advantages, the arrangement herein before described being merely by way of example. In no way is the invention restricted to these specific forms shown or used as mentioned above, except as defined in the accompanying claims.

The inventor claims:

1. A valve comprising:
   an outer valve part comprising a tubular barrel having a relatively large diameter cylindrical portion at one end, a relatively small diameter nipple at the other end, an interior cylindrical wall defined by said relatively large diameter cylindrical portion, and an axial flow metering bore between said ends communicating at one end to the interior of said cylindrical portion and at the other to an axial passage through said nipple;
   an inner valve part comprising a sleeve having an axial flow metering plug at one end slidably fitting in said metering bore, a cylindrical coupling portion at the other end, a threaded portion adjacent said cylindrical coupling portion, and a radial axially presented transverse wall about said plug between said plug and said threaded portion, said metering plug and axial flow metering bore defining therebetween at least one tapered axially extending flow passage, whereby relative axial adjustment between said metering plug and axial flow metering bore regulates fluid flow through said metering bore;
   means to prevent relative rotation between said outer and inner valve parts; and a collar threadably connected to said inner valve part, said collar including rotatably sliding attachment means to said outer value part whereby rotation of said collar causes relative axial movement of said metering plug and axial flow metering bore.

2. The valve as defined in claim 1 wherein:
   said inner valve part includes a seal member thereabout, said seal member having a pair of circumferential sealing ribs spaced a predetermined distance apart which is greater than the possible relative axial movement of said inner and outer valve parts, said ribs being sized and positioned to seal against said cylindrical interior wall of said outer valve part.

3. The valve as defined in claim 2 wherein:
said inner valve part includes a pair of spaced radially extending rings between which said seal member is retained.

4. The valve as defined in claim 3 wherein:
said tapered axial flow passage is defined by said axial flow metering bore.

5. The valve as defined in claim 3 wherein:
said tapered axial flow passage is defined by said plug.

6. A valve having a flow passageway therethrough for controlling the flow of fluid in an intravenous flow line including:
means for connecting said valve to a source of the fluid;
means for connecting said valve to a receiver of said fluid;
a first valve portion having an axis and defining at least a portion of said flow passageway therethrough;
a second valve portion defining at least a portion of said flow passageway therethrough;
means to control the flow of fluid through said valve which depend on the relative axial positioning of said first and second valve portions; and
means to vary the relative axial positioning of said first and second valve portions including a threaded portion on said first valve portion, a collar threadably engaged with said threaded portion of said first valve portion and radially slidably engaged with said second valve portion, and means to prevent relative rotation between said first and second valve portions.

7. The valve as defined in claim 6 wherein:
said means to prevent relative rotation between said first and second valve portions include at least one axially aligned channel formed in one of said valve portions and at least one radially oriented projection extending from the other valve portion into said channel.

8. The valve as defined in claim 7 wherein:
said channel is formed on said second valve portion and said radially oriented projection extends outwardly from said first valve portion.

9. The valve as defined in claim 8 wherein:
said collar includes at least one axially extending tang having a lip surface thereon and wherein said second valve portion has a radial ring surface thereon positioned for engagement by said tang lip for sliding engagement therewith.

10. The valve as defined in claim 9 wherein:
said collar includes a radial abutment surface thereon generally facing a direction opposite from said lip surface and said second valve portion includes a radial abutment surface which engages said radial abutment surface of said collar so that said collar is axially restrained to said second valve portion and is free to rotate radially with respect thereto.

11. The valve as defined in claim 10 wherein:
said first and second valve portions include means to restrict axial motion therebetween to a first predetermined distance, said first valve portion including a seal member thereabout, said seal member having a pair of circumferential sealing ribs spaced a second predetermined distance apart which is greater than said first predetermined distance, said ribs being sized and positioned to seal against said outer valve portion.

12. The valve as defined in claim 11 wherein:
said inner valve portion includes a pair of spaced radially extending rings between which said seal member is retained.

13. A valve having a flow passageway therethrough for controlling the flow of fluid in an intravenous flow line including:
means for connecting said valve to a source of the fluid;
means for connecting said valve to a receiver of said fluid;
a first valve portion having an axis and defining at least a portion of said flow passageway therethrough;
a second valve portion defining at least a portion of said flow passageway therethrough;
means to control the flow of fluid through said valve which depend on the relative axial positioning of said first and second valve portions; and
means to vary the relative axial positioning of said first and second valve portions a first predetermined distance, said first valve portion including a seal member thereabout, said seal member having a pair of circumferential sealing ribs spaced a second predetermined distance apart which is greater than said first predetermined distance, said ribs being sized and positioned to seal against said outer valve portion to close said flow passageway to contamination.

14. The valve as defined in claim 13 wherein:
said inner valve portion includes a pair of spaced radially extending rings between which said seal member is retained.

15. The valve as defined in claim 14 wherein:
said means to vary the relative axial positioning of said first and second valve portions a first predetermined distance include:
a threaded portion on said first valve portion;
a collar threadably engaged with said first valve portion and radially slidably engaged with said second valve portion; and
means to prevent relative rotation between said first and second valve portions.

16. The valve as defined in claim 15 wherein:
said means to prevent relative rotation between said first and second valve portions include at least one channel formed in one of said valve portions and at least one radially oriented projection extending from the other valve portion into said channel.

17. The valve as defined in claim 16 wherein:
said channel is formed axially in said second valve portion and said radially oriented projection extends outwardly from said first valve portion.

18. The valve as defined in claim 17 wherein:
said collar includes at least one axially extending tang having a lip surface thereon and wherein said second valve portion has a radial ring surface thereon positioned for engagement by said tang lip for sliding engagement therewith.

19. The valve as defined in claim 18 wherein said collar includes:
a serrated outer radial surface for manual manipulation; and a radial abutment surface thereon generally facing a direction opposite from said lip surface, said second valve portion including:

a radial abutment surface which engages said radial abutment surface of said collar so that said collar is axially restrained to said second valve portion and is free to rotate radially with respect thereto.

20. The valve as defined in claim 19 wherein:
said second valve portion includes indicia thereon which in cooperation with said tang indicates the relative axial positions of said first and second valve portions.

* * * * *